US007201878B2

(12) United States Patent
Lin et al.

(10) Patent No.: US 7,201,878 B2
(45) Date of Patent: *Apr. 10, 2007

(54) AEROSOL PARTICLE ANALYZER FOR MEASURING AN ANALYTE IN AIRBORNE PARTICLES

(75) Inventors: Horn-Bond Lin, Fairfax, VA (US); Steven Clyde Hill, Silver Spring, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 232 days.

This patent is subject to a terminal disclaimer.

(21) Appl. No.: 10/816,579

(22) Filed: Mar. 26, 2004

(65) Prior Publication Data

US 2005/0214168 A1 Sep. 29, 2005

(51) Int. Cl.
*B32B 5/02* (2006.01)
*B32B 27/04* (2006.01)
*B32B 27/12* (2006.01)
*G01N 30/96* (2006.01)
*C12M 1/34* (2006.01)

(52) U.S. Cl. .................. 422/88; 422/82.05; 422/82.08; 422/83; 435/7.1; 435/283.1; 435/288.7; 436/35; 436/36; 436/149; 436/153; 436/172; 436/181; 356/36; 356/37; 356/300; 356/318; 356/335; 250/281; 250/282; 250/283; 250/288; 250/299

(58) Field of Classification Search .................. 436/35, 436/36, 149, 153, 172, 181; 422/83, 88, 422/82.05, 82.08; 435/7.1, 283.1–283.2, 435/288.7; 356/36, 37, 300, 318, 335; 250/281–283, 250/288, 299

See application file for complete search history.

(56) References Cited

U.S. PATENT DOCUMENTS

2005/0179893 A1* 8/2005 Hill ............................ 356/318

* cited by examiner

*Primary Examiner*—Long V. Le
*Assistant Examiner*—Jacqueline A. DiRamio
(74) *Attorney, Agent, or Firm*—A. David Spevack; Stephen Bloor

(57) ABSTRACT

Aerosol particle analyzer (APA) for measuring an analyte in airborne particle is described. Airborne particles are first given an electrical charge and then drawn in air past an oppositely charged volume of an analysis liquid that exposed to the air at a small hole in a container, such as a capillary, that holds that analysis liquid. Electrostatic forces enhance the rate that the airborne particles collide with the small exposed volume of the analysis liquid in the hole. If the particles that collide with the analysis liquid contain the analyte, an optical property of the analysis liquid, such as the fluorescence, varies according to the amount of the analyte in the particles. This optical property is measured and the amount of analyte in the particles is determined from the measured optical property.

23 Claims, 3 Drawing Sheets

AEROSOL PARTICLE ANALYZER FOR MEASURING AN ANALYTE IN AIRBORNE PARTICLES

BACKGROUND OF THE INVENTION

1. Field of the Invention

This invention pertains generally to chemical analytical and immunological testing, and particularly to processes wherein samples are analyzed by using self-operated mechanisms or devices, and more particularly to processes wherein a continuously flowing stream of a sample or carrier fluid is formed and flows into and through analysis, wherein the continuously flowing stream is segmented.

2. Description of the Related Art

Devices are needed that can quickly ascertain and identify the presence of harmful materials in airborne particles. Airborne infectious agents such as bacteria and viruses transmit many diseases of humans, other animals, and plants. Some of these infectious agents, as well as some protein toxins have been used as biological-warfare (BW) agents. Some airborne proteins and pollens cause allergies. Improved methods for characterizing aerosols would be useful for understanding atmospheric chemistry, including the sources, chemical reactions, and fates of atmospheric particles.

Here, "airborne particle" refers to both the solid particles and liquid droplets in an air sample. The analyte is the specific molecule, microorganism, or virus to be identified. For example, for biological warfare (BW) agents that are protein toxins, e.g., ricin, the toxin itself is the analyte. For BW agents that are bacteria or viruses, the analyte can be a molecule that is specific to the bacteria or virus to be detected, e.g., a protein or a DNA or RNA sequence. In this case the amount of the analyte is measured. If this amount is significantly above a noise threshold, the presence of the BW agent is inferred. For BW agents that are bacteria or viruses, the analyte can be the bacteria or virus itself.

Key objectives for some types of instruments needed for detecting BW-agents or other analytes in airborne particles are:

(a) Sensitivity. An instrument should be able to measure and identify small amounts of a BW-analyte in the particles in an air sample, because small amounts of BW agents may be lethal.

(b) Specificity. An instrument should have a very low rate of false positives, i.e., reporting a BW-analyte when it is not in the air sample.

(c) Rapid response. An instrument should have no more than a short delay between the time a BW aerosol enters the instrument and the time the instrument indicates that a BW-analyte has been identified. The sooner people know they are under attack, the sooner they can take protective measures if available, try to leave the region of exposure, or seek medical treatment. Also, with a sufficiently rapid alert some people can avoid exposure altogether.

(d) Continuous operation. An instrument should be able to run essentially continuously for days or weeks at a time. It should run continuously because BW aerosols could appear at any time. Presently, "trigger" instruments, which run continuously but cannot identify BW-agents, are used to tell when to turn on instruments that can identify agents. If there were some "trigger" instrument that was adequate for telling when to turn on an identifier, there would be no need for an identifier. But it is difficult to imagine that any of the reagentless techniques being investigated or suggested for trigger instruments would be able to identify specific BW agents in cases where these BW agents comprise a small fraction of the total particles in a complex mixture of airborne particles, especially if these agents are mixed with other materials before aerosolization.

(e) Little need for consumables. An instrument should not require large amounts of consumables (e.g., liquids, antibodies, microscope slides, filters). The more consumables required the fewer BW-aerosol-detection instruments that can be maintained in continuous operation.

(f) Little need for operator time. If more operator time is required, fewer BW-aerosol-detection instruments can be maintained in continuous operation.

(g) Be able to separate and store particles for further analysis. It is desirable to confirm the detection of analyte using complementary techniques which may be much less rapid.

Investigators have worked for years to develop instruments and methods that are useful for detecting airborne BW agents. Samples can be collected from air using a variety of different collectors, and the collected samples can be subjected to many different types of microbiological and biochemical analyses. Therefore, the number of possible approaches is very large. Because of the importance of the problem, progress is being made, e.g., improved recognition molecules such as antibodies and aptamers for BW agents are being developed; more rapid methods of extracting DNA and RNA from spores are being explored; methods for detecting very small amounts of analytes or very small amounts of antigen-antibody reactions are being improved and new methods are being developed; improved methods of concentrating airborne particles, and collecting them from air are being developed; and instrumentation is being developed to perform the analysis in an automated fashion, for example, an automated flow cytometer has been developed for BW-agent detection.

Some reasons that make it difficult for these objectives to be met simultaneously are as follows. Objectives (a) and (b) require sensitivity and specificity. To measure the amount of an analyte that is a BW agent or is indicative of a BW agent in a complex sample (collected from air or otherwise), requires the sample to be mixed with one or more liquids, termed here, "analysis liquids." At least one of these liquids contains sensor molecules, also termed recognition molecules, that selectively bind to or interacts with the analyte. Example recognition molecules are antibodies and aptamers. Aptamers are DNA or RNA molecules that are selected for their ability to bind to the analyte. As a result of this binding of the recognition molecule to the analyte, some measurable property, e.g., fluorescence, must change according to the amount of analyte in the sample. That property is measured and the amount of analyte is inferred.

Objectives (c) and (d) require continuous operation for days or weeks, and therefore continuous expenditure of consumables. Therefore, because of objective (e) limiting consumables, each measurement must require only a very small amount of consumables. In addition to the consumables used in analyzing the sample, consumables are typically expended in collecting particles from the air to be analyzed.

If the particles are collected on filters or impacted on a surface, the filter or surface is a consumable unless it is cleaned; in which case whatever is used to clean it may be consumed. In typical analysis procedures for biochemical analytes in airborne particles, the airborne particles are collected into a liquid, which tends to evaporate as the sample is collected, especially if the air sample is warm and dry.

The objectives of sensitivity and specificity, suggest choosing as analytes specific DNA or RNA sequences, and this approach may be applicable for some analytes. However, objective (c) for a rapid response makes this approach not feasible for spores because 10's of minutes are required for the DNA from a spore to be extracted, amplified, and detected. Also, this approach is not applicable to BW agents that do not contain DNA or RNA, such as protein toxins.

A recently submitted patent application (Ser. No. 10/708,191, S. C. Hill, Aerosol Particle Analyzer for Measuring the Amount of Analyte in Airborne Particles) aims to achieve these goals simultaneously by colliding in air droplets of an anlaysis liquid with airborne particles, and then levitating these droplets long enough for the reaction between the analysis liquid and the droplet to occur and to be measured.

Recently B cells, which are a type of lymphocyte, have been modified to fluoresce strongly within seconds when they come in contact with specific pathogens such as anthrax, or plague, or viruses (T. H. Rider et al., "A B Cell-Based Sensor for Rapid Identification of Pathogens," Science, 301, 213–215 (2003).

SUMMARY OF THE INVENTION

In consideration of the problems detailed above and the limitations in the partial solutions thereto, an object of the present invention is to provide an improved aerosol particle analyzer (APA) for measuring an analyte in airborne particles. In this invention the term "particles" includes both solid and liquid particles.

Another object of the present invention is to provide an APA that is sensitive to a small number of particles that contain the analyte in a large volume of air.

Yet another object of the present invention is to provide an APA that is specific for the analyte.

Yet a further object of the present invention is to provide an APA that has a rapid response, with no more than a short delay between the time the analyte aerosol enters the instrument and the time the instrument indicates that an analyte has been identified.

Yet another object of the present invention is to provide an APA that can run continuously.

Yet another object of the present invention is to provide an APA that has a low requirement for consumables.

Yet another object of the present invention is to provide an APA that has little need for operator time.

In order to attain the objectives described above, according to an aspect of the present invention, there is provided an aerosol particle analyzer (APA) for measuring an analyte in airborne particles in a gas such as the atmosphere. The APA requires an analysis liquid that has the following property: when the analysis liquid is mixed with particles, the fluorescence of the analysis liquid varies according to the amount of the analyte in the particles, so that the amount of analyte can be determined from measurements of the fluorescence.

To achieve the objective of specificity, the analysis liquid typically requires molecules, such as aptamers, antibodies, nucleic acids, or phage-displayed epitopes that are specific for the analyte. The analysis liquid is in an analysis liquid container (ALC). APA's typically operates as follows. A wire electrode in the ALC is set to a positive potential, and an analysis-liquid pump (ALP) connected to the ACL increases the pressure on the analysis liquid in the ALC, so that a small amount of the analysis liquid 800 protrudes through a hole in the ALC to form a charged-volume of the analysis liquid at the hole (CVALH). A pump draws gas and particles through a charger that imparts a negative charge to the particles, then into an airtight box, then past the CVALH. As the negatively charged particles flow near the CVALH, some of them combine with the positively charged CVALH.

A shield electrode around the hole is given a voltage opposite to that of the CVALH, and of much smaller magnitude than the voltage applied to the CVALH, so that particles are not attracted to this region around the hole, but to the CVALH. If one or more of the particle(s) that mix with the CVALH contain some analyte, the fluorescence of the CVALH changes in accordance with the amount of the analyte.

After a time sufficient for the analyte to react with the analysis liquid and to generate fluorescence, the fluorescence of the CVALH is measured. The amount of the analyte in the particles that collided with the CVALH is determined from this measured fluorescence. Then the ALP increases the pressure on the analysis liquid in the ALC so that a droplet of the analysis liquid is ejected and falls into a receptacle at the bottom of the airtight box. After the droplet of the analysis liquid is ejected, the ALP adjusts the pressure on the analysis liquid so that the CVALH is ready to begin the next measurement. During the time that the particles pass near and are attracted to the CVALH, the volume of the CVALH extending from the hole is kept large by the ALP pumping analysis liquid into the CVALH, so that the total charge on the CVALH is large, such that more of the negatively charged particles are attracted to the CVALH and collide with it.

Other components used in some embodiments of the APA are:

(i) An aerosol particle concentrator that concentrates particles in the air before they enter the charger. It can greatly increase the sensitivity of the APA.

(ii) An aerosol particle counter (APC) that measures the numbers of particles in different size ranges. This APC can be especially useful in cases where it is more probably that nonspecific reactions will occur between the analysis liquid and other molecules that are not the analyte. If such reactions result in changes in fluorescence that appear like those that occur with the analyte, then the sensitivity is reduced, or the false positive rate is increased. The APA must be calibrated so that the mass of the particles that combine with each CVALH can be determined from APC measurements of the particle size and number. Then this measured mass of the particles that combined with the CVALH can be used with the fluorescence measurement of the CVALH to determine the analyte per mass of particles that combined with the CVALH. If a very small fluorescence signal is measured for a small mass of particles, this is far more likely to be analyte than if the same small amount of fluorescence were measured for a relatively large mass of particles.

A novel feature of an embodiment of the APA described in the present invention is the ability to:

(a) collect charged particles from the air efficiently into a very small volume of the analysis liquid, i.e., into the small volume of analysis liquid at a small hole, as on the end of a capillary tube, while the air is flowing somewhat rapidly past the end of this small volume of liquid so that a large number of particles can collide with the CVALH, and (b) hold this small volume of the analysis liquid for the time required for the analyte to react with the analysis liquid and for the change in fluorescence to be detected.

The aforementioned features, objects, and advantages of this method over the prior art will become apparent to those skilled in the art from the following detailed description and accompanying drawings.

DETAILED DESCRIPTION OF THE PREFERRED EMBODIMENTS

Figure 1:
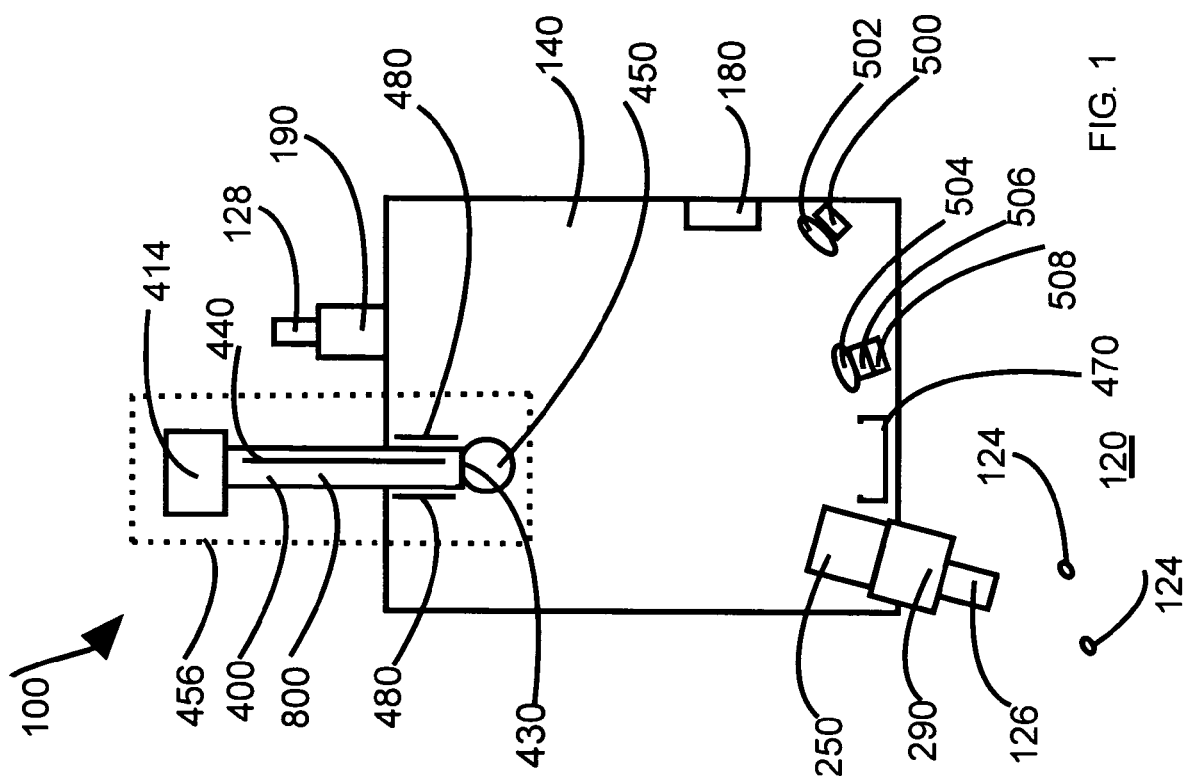
FIG. 1 is a schematic illustration of one embodiment of the APA.

Referring to FIG. 1, an aerosol particle analyzer (APA) 100 is immersed in a gas 120, such as the atmosphere, having particles 124 therein. Generally, the particles 124 include many types of particles 124, some of which may contain no analyte 80, and some of which may contain some amount of the analyte 80. The particles 124 may be liquid, solid, or a mixture of liquid and solid.

An analysis liquid 800 is in an analysis-liquid container (ALC) 400. The analysis liquid 800 is chosen to have the following property: when the analysis liquid 800 is mixed with particles 124, the fluorescence of the analysis liquid 800 varies according to the amount of the analyte 80 in the particles 124, so that the amount of analyte 80 can be determined from measurements of the fluorescence.

Figure 3:
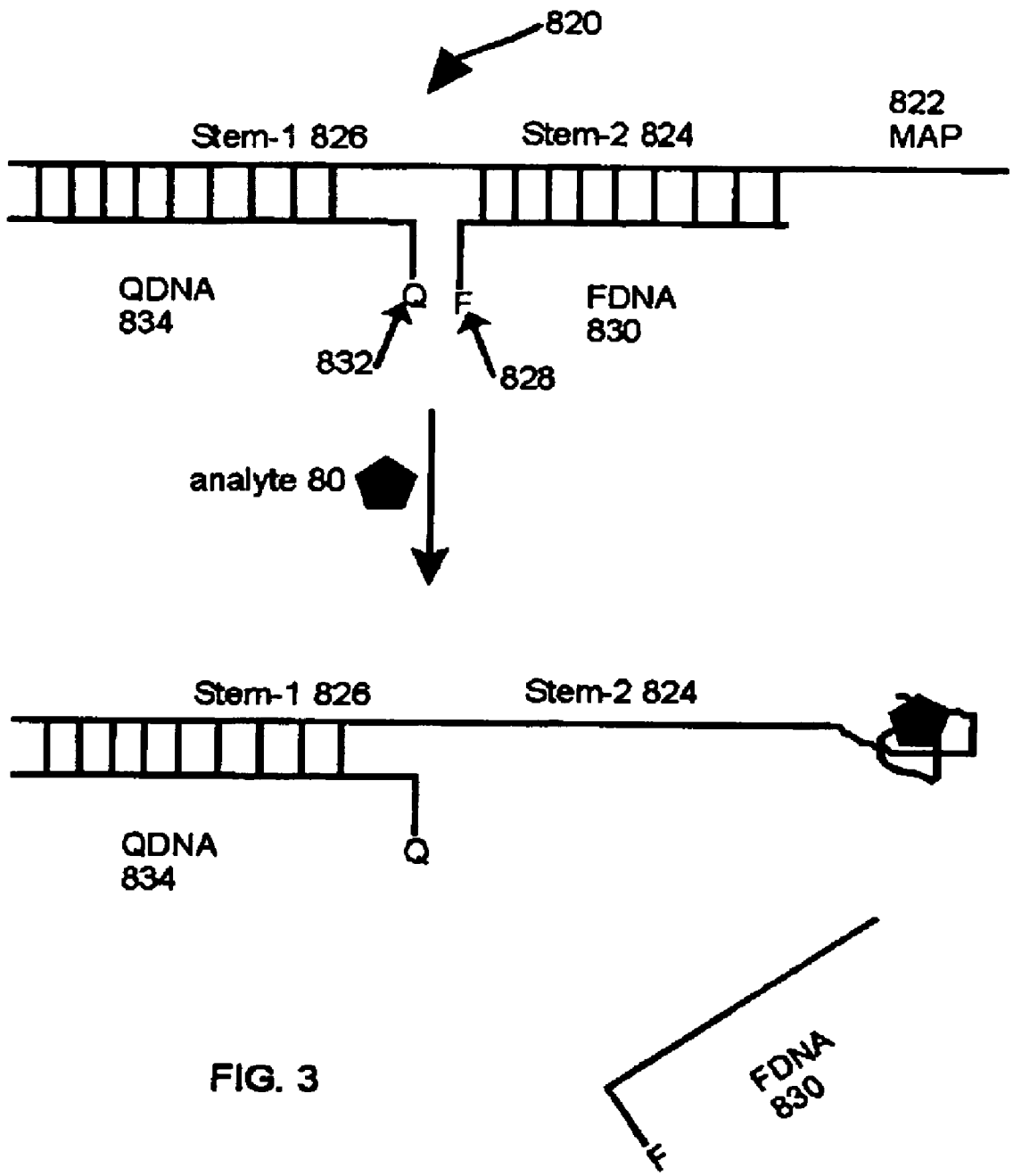
FIG. 3 illustrates schematically an embodiment of the reaction that takes place in the charged volume of the analysis liquid at the hole when analyte is present in a particle that collided with the droplet.

The measurement of the analyte 80 in the particles 124, as shown in FIG. 3, is accomplished as follows. A wire electrode 440 in the ALC 400 is set to a positive potential, and an analysis-liquid pump (ALP) 414 connected to the ACL 400 increases the pressure on the analysis liquid 800, so that a small amount of the analysis liquid 800 protrudes though a hole 430 in the ALC 400 to form a charged-volume of the analysis liquid at the hole (CVALH) 450. A pump 190 creates a vacuum in an airtight box 140 and thereby draws gas 120 and particles 124 through an induction port 126, then into a article counter 290 that counts the counts the particles entering the APA 100, then into a charger 250 that imparts a negative charge to the particles 124, then into an airtight box 140, then past the CVALH 450, and then exhausts at least the gas 120 out of an exit port 128. As the gas 120 and particles-124 flow though the aittight box 140, at least some of the particles 124 collide with the CVALH 450 and combine with it so that the analyte 80 in the particles 124 can be measured. Electrostatic forces increase the fraction of the particles 124 that combine with the CVALH 450. The particles 124 are given a negative charge by the charger 250 so that they are drawn toward the positivley charged CVALH 450 by electostatic forces. When the CVALH 450 is negatively the particles 124 are given a positive charge by the charger 250 so they are drawn to the CVALH 450. A shield electrode 480 around the hole 430 is given a voltage oppsite to that of the CVALH 450, and of much smaller magnitude than the voltage applied to the CVALH 450, so that particles are not attacted to this region around the hole 430, but to the CVALH 450. More than one particle 124 may combine with the CVALH 450. If one or more of the partile(s) 124 that mix with the CVALH 450 contain some analyte 80, the fluorescence of the CVALH 450 begins to change in accordance with the amount of the analyte 80. After a time sufficient for the analyte 80 to react with the analysis liquid 800 and to generate fluorescence, the fluorescence of the CVALH 450 is measured as explained below. The amount of the analyte 80 in the particles that collided with the CVALH 450 is determined from this measured fluorescence. Then the ALP 414 increases the pressure on the analysis liquid 800 in the ALC 400 so that a CVALH 450 is ejected and falls into a receptacle 470 at the bottom of the airtight box 140.

After the CVALH 450 is ejected, the ALP 414 adjusts the pressure on the analysis liquid so that a new CVALH 450 is ready to begin the next measurement. The fluorescence is measured by illuminating the CVALH 450 with light from at least one light source, such as, for example, the laser diode 500 that is focused by a laser-diode lens 502 in FIG. 1, and detecting the fluorescence with a photodetection means such as that shown in FIG. 1, where the fluorescence is (i) collected with a photodetector lens 504, (ii) filtered with a photodetector filter 506, and (iii) measured with a photodetector 508.

In the preferred embodiment, during the time that the particles 124 pass near and are attracted to the CVALH 450, the volume of the CVALH 450 extending from the hole 430 is kept large, so that the total charge on the CVALH 450 is large, so that more of the negatively charged particles 124 are attracted to the CVALH 450 and collide with it. As water evaporates from the CVALH 450, the ALP 414 pumps more analysis liquid 800 into the CVALH 450 to keep it large. When it is time to measure the fluorescence, the CVALH 450 is allowed to evaporate to a small volume so that it protrudes only a little from the hole 430, so that the fluorescent molecules are more concentrated and can be read with a better signal to noise ratio, and additionally so that the curved surface of a large CVALH 450 does not complicate the measurement of the fluorescence.

By using only a small amount of the analysis liquid 800 for each measurement, the APA 100 satisfies one objective of the APA 100. By ejecting the CVALH 450 at the end of each measurement, the APA 100 washes the analysis liquid that combined with the particles 124 out of the ALC 400 so that it minimizes cross contamination and reduces the need for replacing expendable items, thereby satisfying another objective of the APA 100.

The humidity and temperature of the gas 120 in the APA 100 are measured by a humidity-temperature sensor 180 so that the measured humidity and temperature can be used, with the help of look up tables, to: (i) determine the amount of water that will evaporate from the CVALH 450 prior to the measurement, so that the analysis liquid 800 can be prepared with the required concentrations of solutes to compensate for any water that evaporates from the CVALH 450 during the time prior to the measurement of fluorescence, so that the ionic strength of the analysis liquid at the time of measurement is as required, and (ii) determine the amount of additional analysis liquid 800 the ALP 414 needs to pump into the CVALH 450 in order to keep the CVALH 450 large during the time when the particles 124 are drawn to and collide with the CVALH 450 so that more particles can be drawn to the CVALH 450, and to determine when the ALP 414 should stop pumping analysis liquid 800 into the CVALH 450 so that the CVALH 450 can evaporate until it is small enough that it protrudes relatively little from the hole 430 while the fluorescence is measured, so that the fluorescence can be measured more accurately.

A particle counter 290 measures the concentrations of particles 124 in different size ranges drawn into the APA 100 so that when the APA 100 is calibrated the mass of the particles 124 that combine with the CVALH 450 can be estimated from a lookup table, so that the concentration of the analyte 80 in the particles can be determined from the measurements of the amount of analyte 80 in the particles 124 and the estimated mass of the particles 124 that combined.

The ALC 400 with the hole 430, the ALP 414, and the electrode 440 with the shield electrode 480 together comprise the analysis-liquid handling subsystem (ALHS) 456. In one exemplar, the ALC 400, near the hole 430, is circular as in a typical capillary tube.

In one exemplar, the polarity of voltage of the CVALH 450 is positive for one measurement, negative for the next measurement, positive for the next measurement, and so on, so that if there are differences in the tendency for a type of particle 124 to accept either a positive or a negative charge, or to be modified by the charging process in a polarity-dependent manner, these differences will be apparent in the results of the measurements.

Figure 2:
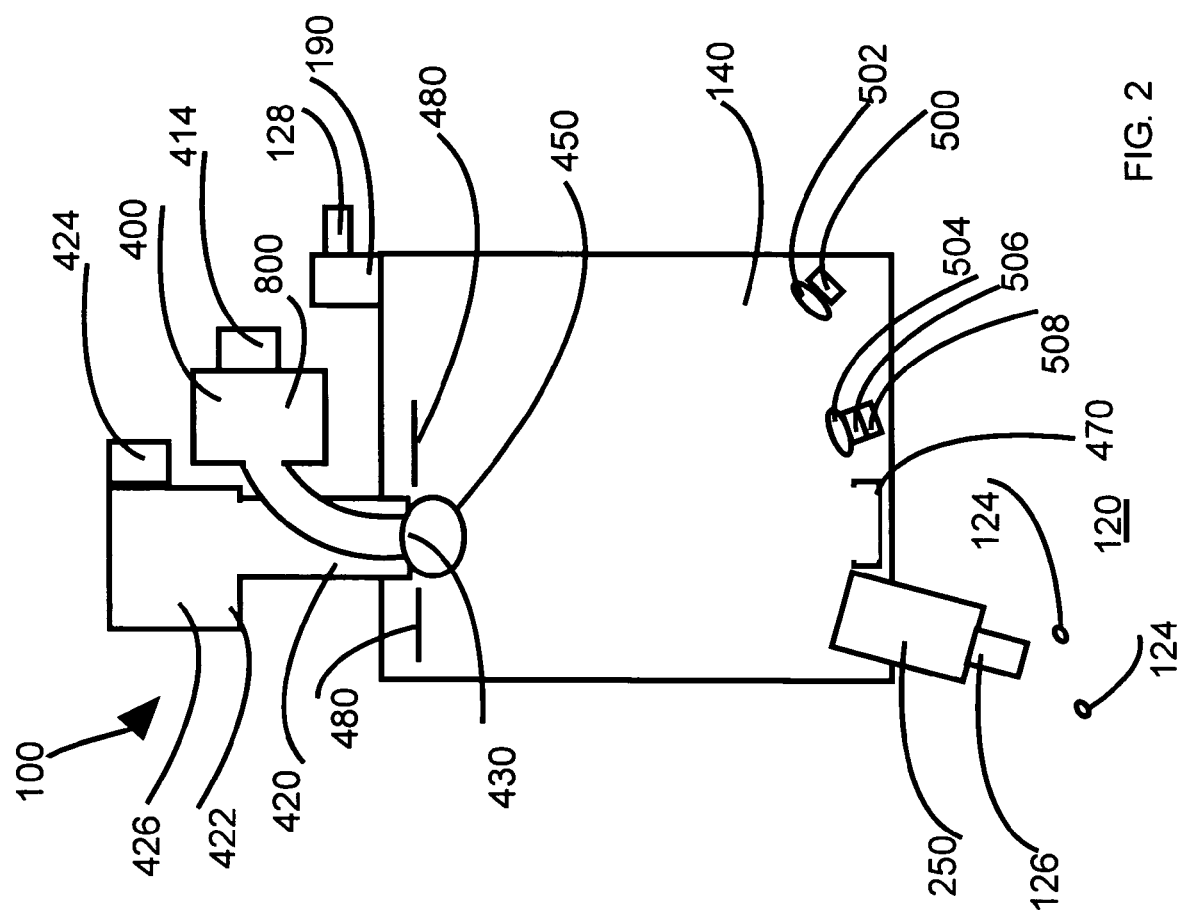
FIG. 2 is a schematic illustration of another embodiment of the APA with concentric capillary around the central tube.

FIG. 2 illustrates another embodiment, one in which the ALC 400 near the hole 430 has the shape of capillary tube, and the ALC 400 near the hole 430 is surrounded by a capillary sheath 420. The capillary sheath 420 is connected to a water reservoir 422 that holds water 426. A water pump 424 is connected to the water reservoir 422 so that the water pump 424 can vary the pressure of the water 426 in the sheath 420, so that it also can replenish any water that evaporates from the CVALH 450 during a measurement. In the preferred embodiment, during the time that the particles 124 pass near and are attracted to the CVALH 450, the CVALH 450 is kept large so that the total charge on the CVALH 450 is large, so that more of the negatively charged particles 124 are attracted to the CVALH 450 and collide with it. As water evaporates from the CVALH 450, liquid water is pumped through the capillary sheath 420 to keep the CVALH 450 large. When it is time to measure the fluorescence, the CVALH 450 is allowed to evaporate to a small volume, so that it protrudes only little from the hole 430 at the end of the ALC 400, so that the fluorescent molecules are more concentrated and can be read with a better signal to noise ratio, and so the curved surface of the large CVALH 450 does not complicate the measurement of the fluorescence. The water reservoir 422 may contain a water solution that contains additional molecules, so that a two-step reaction for detection of the analytes may be employed.

In one embodiment particles are charged using a commercially available ionizer, such as the AS 150 MM supplied by Wein Products, Inc., Los Angeles, Calif., which was used by G. Mainelis, K. Willeke, A. Adhikari, T. Reponen, and S. A. Grinshpun, "Design and Collection Efficiency of a New Electrostatic Precipitator for Bioaerosol Collection," Aerosol Science and Technology, 36, 1073–1085 (2002), especially pp. 1074–1075, herein incorporated by reference. In one embodiment the charger 250 is of the corona-discharge type as described by R. Vehring, C. L. Aardahl, G. Schweiger and E. J. Davis, "The characterization of fine particles originating from an uncharged aerosol: size dependence and detection limits for Raman analysis," Journal of Aerosol Science, 29, 1045–1061 (1998), especially pp. 1048–1050, and p. 1057, and by C. L. Aardahl, et al., Electrodynamic trapping of aerocolloidal particles: experimental and theoretical trapping limits," Journal of Colloid and Interface Science, 192, 228–237 (1997), both herein incorporated by reference, especially pp. 231–233 of the second reference.

In another preferred embodiment, alternating-current corona charging is used to impart more charge per particle 124 with fewer particles 124 lost, as described by M. Lakowski, "Unipolar charging of aerosol particles in alternating electric field," Journal of Electrostatics, 51–52, 225–231 (2001), especially FIG. 2 on page 228 of that paper and the description of the apparatus on pp. 227 and 228, both of which are herein incorporated by reference. The greater charge on the particles 124 generated with alternating current charging leads to a higher fraction of the particles 124 colliding with the CVALH 450 and being analyzed.

In another preferred embodiment, the electrospray ionization apparatus described by John B. Fenn in "Electrospray Air Sampler," US Patent Application Publication 2004/0023411 A1, herein incorporated by reference, is used to charge the particles. In one exemplar, the Fenn apparatus is used as the charger 250, but the airflow speed through the charger 250 is greater than it is in Fenn's application so that the particles are carried in the airflow toward the CVALH 450 and do not become caught by the charger 250. By varying the voltages applied to the CVALH 450 and to Fenn's electrode (which in Fenn's FIG. 1 is below the "target collection surface"), one skilled in the art could find a voltage for the CVALH 450 that is relatively large, so that the particles 124 are attracted to it, and so that at least a large fraction of the electric field lines going to Fenn's nozzle originate on the CVALH 450, but not so large that electrospray from the CVALH 450 is generated.

FIG. 3 illustrates schematically one embodiment of the reaction that takes place in the CVALH 450 when analyte 80 is present in the particle 124 that combined with the CVALH 450. FIG. 3 shows how the fluorescence of the analysis liquid 800 changes, so that the fluorescence of the CVALH 450 varies with the amount of analyte 80 in the particles 124 that combined with the CVALH 450. The example shown in FIG. 3 is the same as that shown in FIG. 6A of an article by R. L. Nutiu and Y. F. Li, "Structure-switching signaling aptamers," Journal of the American Chemical Society, 125, 4771–4778 (2003), (herein incorporated by reference, especially FIG. 6A). In FIG. 3, the structure-switching signaling aptamer 820 is comprised of: (i) an aptainer (MAP) 822 chosen because it binds selectively to the analyte 80, i.e., it acts as a sensor molecule, (ii) a DNA oligonucleotide, Stem-2_824, which is covalently linked to the MAP 822; (iii) a DNA oligonucleotide, Stem-1_826 that is covalently linked to Stem-2 824; (iv) a fluorophore (F) 832; (v) DNA oligonucleotide (FDNA) 834 that is linked to the fluorophore 832; (vi) a quencher (0) 828; and (vii) a DNA oligonucleotide (QDNA) 830 that is linked to the quencher 828.

The FDNA 834 forms the DNA duplex with Stem-1_826. The QDNA 830 forms the DNA duplex with Stem-2_824. In this structure-switching signaling aptamer 820, the fluorophore 832 and the quencher 828 are held near each other and the quencher 828 quenches the fluorescence of the fluorophor 832, so that the fluorophor 832, fluoresces very weakly if at all. When the analyre 80 is present, the MAP 822 of the structure switching signaling aptamer 820 binds to the analyte 80 as illustrated in FIG. 3, and thereby releases the QDNA 830 so that the fluorophore 832 is no longer quenched, and can fluoresce brightly. In another exemplar, for cases where the analyte 80 is an oligonucleotide, the approach illustrated in FIG. 3 is used, but for these analytes 80 the aptamer (MAP) 822 is replaced by an oligonucleotide that is complementary to the analyte 80. In another exemplar, the analysis liquid contains a molecular aptamer beacon as described by J. W. L. Li, X. H. Fang and W. H. Tan in, "Molecular Aptamer Beacons for Real-time Protein Recognition," Biochemical and Biophysical Research Communications, 292 (I), 31–40 (2002), incorporated herein by reference. A description of methods for generating and using aptamers and molecular beacon aptanlers is in U.S. Pat. No. 6,531,286 B2, "Homogeneous detection of a target through nuclic acid ligand-ligand beacon interactions," by S. Jayasena and L. Gold. In other exemplars, the sensor molecule may be, an antibody or a phage-displayed epitope or another protein, or it may be a nucleic acid selected to bind to a DNA or RNA sequence from the analyte organism.

In another exemplar, the APA 100 is as in FIG. 1, but it does not have the charger 250. Atmospheric particles typically carry only a small charge, so the collection efficiency of this exemplar is lower than the embodiments that include a charger 250. However, airborne microorganisms tend to carry a negative charge, at least relatively soon after aerosolization (see G. Mainelis, K. Willeke, P. Baron, S. A. Grinshpun, and D. Reponen, "Induction Charging and Electrostatic Classification of Micrometer-Size Particles for Investigating the Electrobiological Properties of Airborne Microorganisms," Aerosol Science and Technology, 36, 479–491 (2002), herein incorporated by reference). Mainelis et al., show that aerosolized sodium chloride tends to carry relatively little intrinsic charge (FIGS. 6, 7a and 8a of Mainelis et al.), but that aerosolized bacteria tend to carry many times as many negative charges (FIGS. 5, 7a and 8a of Mainelis et al.).

We surmise, then, that BW agents may be dispersed in such a way that they carry more charge than typical atmospheric aerosols and so, when the APA 100 is used without any charger 250, or with no voltage applied to the charger 250, the fraction of particles 124 that collide with the CVALH 450 that are biological may be relatively large, especially when the CVALH 450 is given a positive charge, and especially if the biological particles had recently been aerosolized. However, most particles, even most biological particles, would still carry less charge than they do after passing through a charger, and so the efficiency of collection for particles that pass through an efficient charger 250 will tend to be significantly larger.

Although only the measurement of the fluorescence intensity is described here in detail, other fluorescence properties such as the fluorescence polarization, the fluorescence spectrum, and the fluorescence lifetime can also be used in some embodiments of the APA 100, and methods for measuring these properties are well enough known, that more does not need to be stated here. Also, methods for measuring other optical properties such as light scattering properties related to, for example, the measured polarization, spectral intensity, and angular-dependent intensity, have been described by other researchers. Although only the measurement of one analyte is described here in detail, the extension to the measurement of multiple analytes using multiple recognition molecules and multiple fluorophors that have different emission spectra is similar enough to what has been done in other analyses. Also, multiple recognition molecules can be used to detect multiple sites on the same analyte, as is well known. The use of electrostatic forces to deflect charged particles or droplets into different containers, depending upon some measured property of the droplet, e.g., using chargeable deflection plates, is known and has been used with flow cytometry; the sorting of charged droplets of the analysis liquid 450 using electrostatic deflection after they are ejected can also be used with this invention.

Although various preferred embodiments of the present invention have been described herein in detail to provide for complete and clear disclosure, it will be appreciated by those skilled in the art that variations may be made thereto without departing from the spirit of the invention or the scope of the appended claims.

We claim:

1. An aerosol-particle analyzer (APA) for measuring an analyte in particles in a gas comprising:
    (a) an analysis liquid chosen such that when the analysis liquid is mixed with the particles, an optical property of the analysis liquid varies according to the amount of the analyte in the particles;
    (b) an analysis-liquid-handling subsystem (ALHS) consisting of an analysis-liquid container (ALC) that holds the analysis liquid, a pump that is connected to the ALC and that controls the pressure of the analysis liquid in the ALC, a small hole in the ALC through which the analysis liquid can be expelled from the ALC by increasing the pressure in the ALC and can be drawn back into the receptacle by decreasing the pressure in the ALC, an electrode that is in contact with the analysis liquid in the ALC and that is used to control the electrical potential of the analysis liquid, and a shield electrode around the hole that is given a potential opposite that of the analysis liquid, that:
        (i) holds a charged volume of the analysis liquid at the hole in the ALC (CVALH) so that particles in a gas, especially particles that are charged opposite to the voltage of the CVALH, can collide with the CVALH and react with it so the optical property of the analysis liquid can be measured, and the amount of analyte can be determined, and
        (ii) ejects a small volume of the analysis liquid and thereby generates a new CVALH so that the next measurement can take place,
    (c) a charger that imparts a charge to airborne particles drawn through it;
    (d) a substantially gas-tight container, having a gas-tight connection to the ALHS such that the CVALH extends into the gas-tight container so that it is exposed to the gas and particles inside the gas-tight container, a gas-tight connection to the charger, through which gas and charged particles enter the gas-tight container where said gas-tight connection and charger are positioned such that the gas and particles pass near the CVALH, and a vacuum connection;
    (e) a vacuum pump connected to the vacuum connection of the gas-tight container that draws the gas and particle into the gas-tight container through the input and past the CVALH so that the particles can collide with the CVALH, and draws any the gas and particles that did not collide with the CVALH out through the vacuum connection;
    (f) a means to measure changes in the optical property of the CVALH so that the amount of analyte in the particles that combined with the CVALH can be determined from these measurements of the optical property; and
    (g) a collection vessel to collect and store the droplet ejected from the hole after the optical property of the CVALH has been measured.

2. The APA of claim 1 wherein the optical property is a fluorescence property chosen from a group consisting of the fluorescence intensity, the fluorescence polarization, the fluorescence spectrum, and the fluorescence lifetime.

3. The APA of claim 1 wherein the optical property is a light scattering property chosen from a group consisting of the intensity, polarization, spectral intensity, and angular-dependent intensity.

4. The APA of claim 1 wherein the analysis liquid is a water solution that contains sensor molecules that selectively bind to the analyte.

5. The APA of claim 4 wherein the sensor molecule is protein.

6. The APA of claim 4 wherein the sensor molecule is an aptamer.

7. The APA of claim 4 wherein the sensor molecule is phage-displayed epitope.

8. The APA of claim 4 wherein the sensor molecule is a nucleic acid.

9. The APA of claim 1 wherein the analysis liquid contains B cells modified to emit light when they come in contact with the analyte.

10. The APA of claim 1 wherein the charger generates a corona discharge.

11. The APA of claim 1 wherein the charger is an electrospray apparatus.

12. The APA of claim 1 wherein said APA further includes a temperature sensor and a humidity sensor, so that the measured temperature and humidity of the gas in the airtight container can be used to determine the rate the pump pumps and the rate the analysis liquid moves through the hole.

13. The APA of claim 1 further including a reservoir of water, a water pump, and a tube that connects the reservoir of water to the CVALH so that any water that evaporates from the CVALH can be replenished during the measurement time so that the ionic strength of the analysis liquid can be maintained.

14. The APA of claim 13 further including in the water in the reservoir of water, additional molecules suitable for a two-step reaction for detection of the analyte.

15. The APA of claim 1 further including an aerosol particle counter to measure the concentration of, and sizes of, particles in the gas so that the numbers and sizes of particles that combine with the CVALH can be determined approximately by using calibration data.

16. The APA of claim 1 wherein the analysis liquid further contains an additional sensor molecule that selectively binds to an additional region of the analyte.

17. The APA of claim 16 wherein when the additional sensor molecule binds to the additional region of the analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional region of the analyte.

18. The APA of claim 1 wherein the analysis liquid further contains an additional sensor molecule that selectively binds to an additional analyte.

19. The APA of claim 18 wherein, when the additional sensor molecule binds to the additional analyte, the fluorescence of an additional fluorophore changes, and wherein the spectral peak of the fluorescence emission that changes when the sensor molecule binds to the analyte is different from the spectral peak of the fluorescence emission that changes when the additional sensor molecule binds to the additional analyte.

20. The APA of claim 19 wherein said APA further includes a means to measure multiple optical properties of one CVALH.

21. The APA of claim 1 wherein said APA further includes a means to open the container and remove and replace the receptacle, so that the droplets, or what remains from the droplets after the water has evaporated, can be further analyzed.

22. The APA of claim 1 further including an aerosol particle concentrator connected between the inlet and the charger, wherein said concentrator concentrates the particles before they enter the charger so that the APA is sensitive to particles which contain lower concentrations of analyte and to lower concentrations of particles that contain the analyte.

23. The APA of claim 1 wherein said APA further includes a means to sort, by using electrostatic forces, the droplets ejected from the end of the capillary into different receptacles according to the measured value of the optical property.

* * * * *